(12) United States Patent
Dashefsky et al.

(10) Patent No.: US 8,571,893 B2
(45) Date of Patent: Oct. 29, 2013

(54) CLINICAL DATA MONITORING AND ALARMING APPARATUS AND METHODS

(75) Inventors: Michael Dashefsky, Mission Viejo, CA (US); Neal Sanders, Franklin, TN (US)

(73) Assignee: Nihon Kohden America, Inc., Foothill Ranch, CA (US)

( * ) Notice: Subject to any disclaimer, the term of this patent is extended or adjusted under 35 U.S.C. 154(b) by 298 days.

(21) Appl. No.: 13/102,761

(22) Filed: May 6, 2011

(65) Prior Publication Data

US 2011/0275905 A1 Nov. 10, 2011

Related U.S. Application Data

(60) Provisional application No. 61/332,650, filed on May 7, 2010.

(51) Int. Cl.
*G06Q 10/00* (2012.01)
*A61B 5/00* (2006.01)

(52) U.S. Cl.
USPC .............................................. 705/3; 600/301

(58) Field of Classification Search
USPC ............................................................ 705/3
See application file for complete search history.

(56) References Cited

U.S. PATENT DOCUMENTS

2010/0286607 A1* 11/2010 Saltzstein ................... 604/93.01
2011/0172504 A1*  7/2011 Wegerich ...................... 600/301

* cited by examiner

*Primary Examiner* — Hiep V Nguyen

(74) *Attorney, Agent, or Firm* — Shimokaji & Associates, P.C.

(57) ABSTRACT

Clinical data monitoring and alarming devices may have enhanced sensitivity by using sliding median filters on a clinical data stream. This enhanced sensitivity may be realized without introducing an increase in false negative alarm activation.

16 Claims, 3 Drawing Sheets

CLINICAL DATA MONITORING AND ALARMING APPARATUS AND METHODS

CROSS-REFERENCE TO RELATED APPLICATIONS

This application claims the benefit of priority of U.S. provisional patent No. 61/332,650, filed May 7, 2010, the contents of which are herein incorporated by reference.

BACKGROUND OF THE INVENTION

The present invention generally relates clinical data monitors and methods for monitoring clinical data and, more specifically, to clinical data monitoring apparatus and methods that may activate an alarm when the clinical data is measured outside of predefined ranges.

Current clinical data monitoring and alarming systems measure clinical data and issue alarms if the data does not achieve a predetermined minimum quality and/or quality. Conventional systems, however, may yield false positive alarm states due to any number of reasons. For example, a disconnected lead may result in poor or inadequate data, resulting in an alarm state that is not reflective of the patient's actual condition.

As can be seen, there is a need for a clinical data monitoring apparatus and method that can enhance the sensitivity for detecting and alarming on clinical events in a patient while reducing or eliminating false positives without introducing an increase in false negatives.

SUMMARY OF THE INVENTION

In one aspect of the present invention, a clinical data monitoring system comprises a sliding median filter assembly disposed for receiving a data stream over a predetermined time interval, the data stream corresponding to at least one vital sign of a patient being monitored, the median filter assembly being operable on the data stream to determine the presence or absence of a predetermined quantity and quality of the data, and to output a mean value of the data stream corresponding to the vital sign when the predetermined quantity and quality of the data is achieved; a comparative filter disposed for receiving and comparing the mean value output by an algorithm to predetermined data limits; and an alert engine disposed for issuing an alarm when the comparative filter has determined that the mean value output is outside of the predetermined data limits.

In another aspect of the present invention, a method for monitoring clinical data comprises measuring at least one vital sign of a patient; electronically passing a data stream containing the vital sign through a sliding median filter; outputting a mean value of the data stream corresponding to the vital sign, when a proper quantity and quality of data within the data stream is determined; comparing the mean value output to predetermined data limits; and issuing an alarm when the mean value output is outside of the predetermined data limits.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention provide apparatus and methods for enhancing the sensitivity of clinical data monitoring and alarming devices. The apparatus and methods of the present invention may provide this enhanced sensitivity without introducing an increase in false negatives, by using median filters and algorithms, as described in more detail below.

Figure 1:
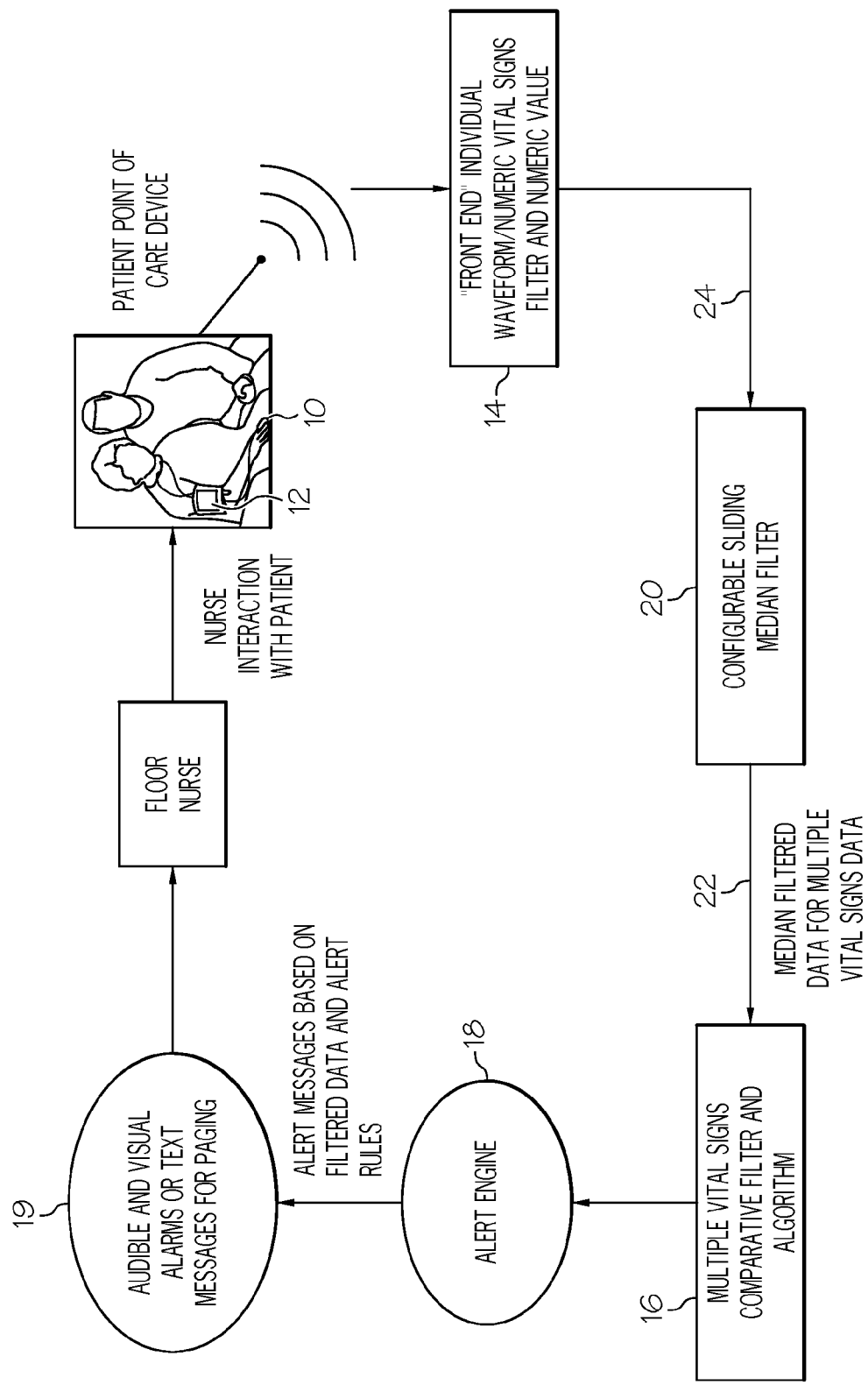
FIG. 1 is a block diagram showing overall system data flow, according to an embodiment of the present invention.

Referring to FIG. 1, there is shown a block diagram outlining data flow in a clinical monitoring system. Patients 10 may wear a device 12, as is known in the art, that may measure vital signs and send an electronic representation thereof, as represented by block 14, as an input to a configurable sliding median filter assembly 20. The filter assembly 20 may provide an output 22 of a median filtered data stream for multiple vital sign data. This output 22 may pass through a comparative filter 16 to compare the vital sign data to predetermined limits. If the data is out of the predetermined limits, an alert engine 18 may generate an alert 19. The clinical monitoring system may include hardware components, such as computing devices, and/or software components. For example, the filter assembly 20 may include software configured to provide the output 22 of the median filtered data stream. The software may be configured to perform certain algorithms, as described in greater detail below.

Figure 2:
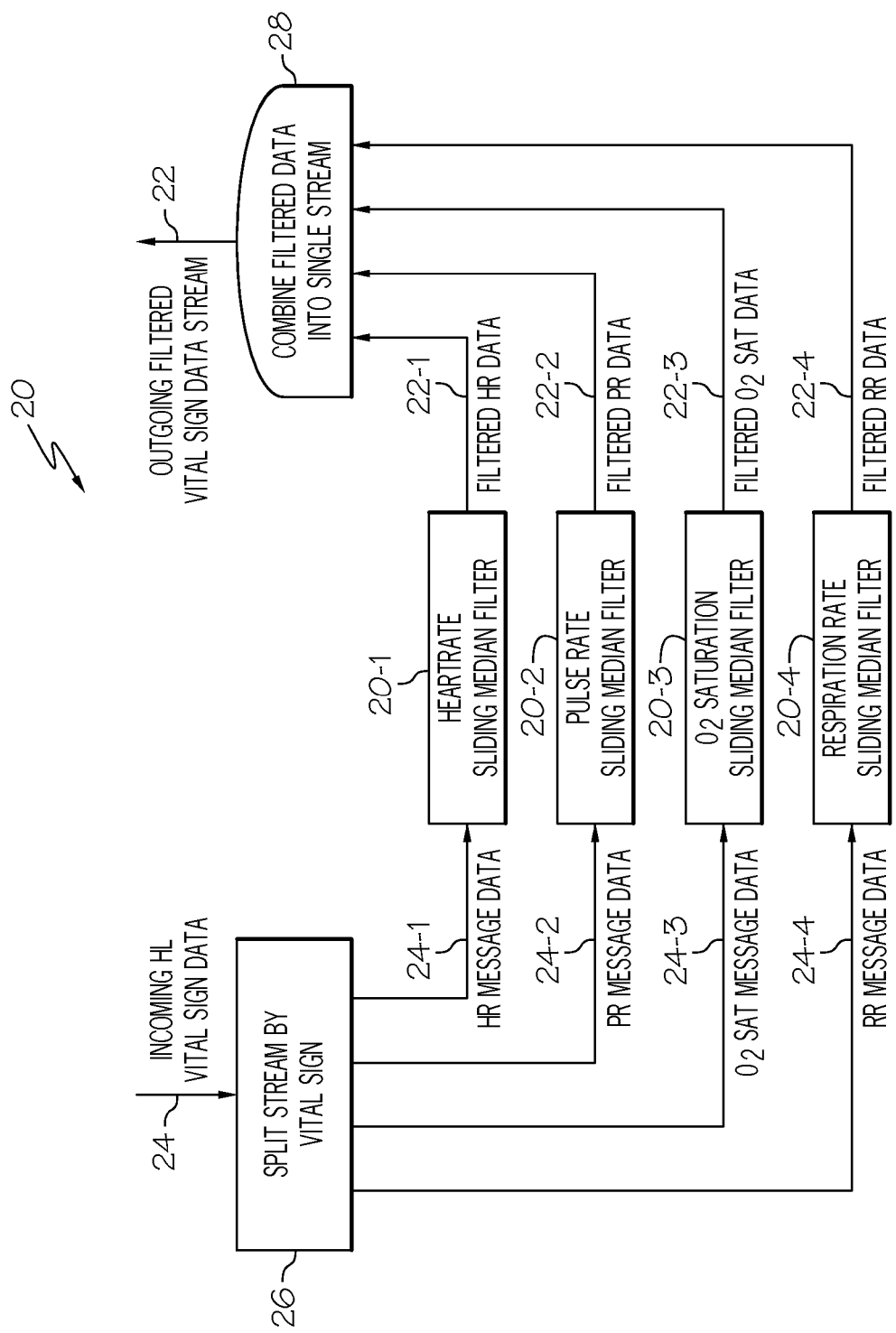
FIG. 2 is a block diagram illustrating use of configurable sliding median filter assembly in the embodiment of FIG. 1.

Referring to FIG. 2, there is shown a block diagram illustrating use of the configurable sliding median filter assembly 20. The filter assembly 20 may receive an input 24 which may be split out into various components at block 26. For example, block 26 may separate the single input 24 into multiple data streams, representing various vital signs, such as a heart rate data stream 24-1, a pulse rate data stream 24-2, an oxygen saturation (pulse ox) data stream 24-3, and a respiration rate data stream 24-4. These data streams may pass through respective sliding median filters 20-1, 20-2, 20-3 and 20-4 to provide respective filtered data streams 22-1, 22-2, 22-3 and 22-4. The filtered data streams 22-1, 22-2, 22-3 and 22-4 may be combined into a single output 22 at block 26.

Figure 3:
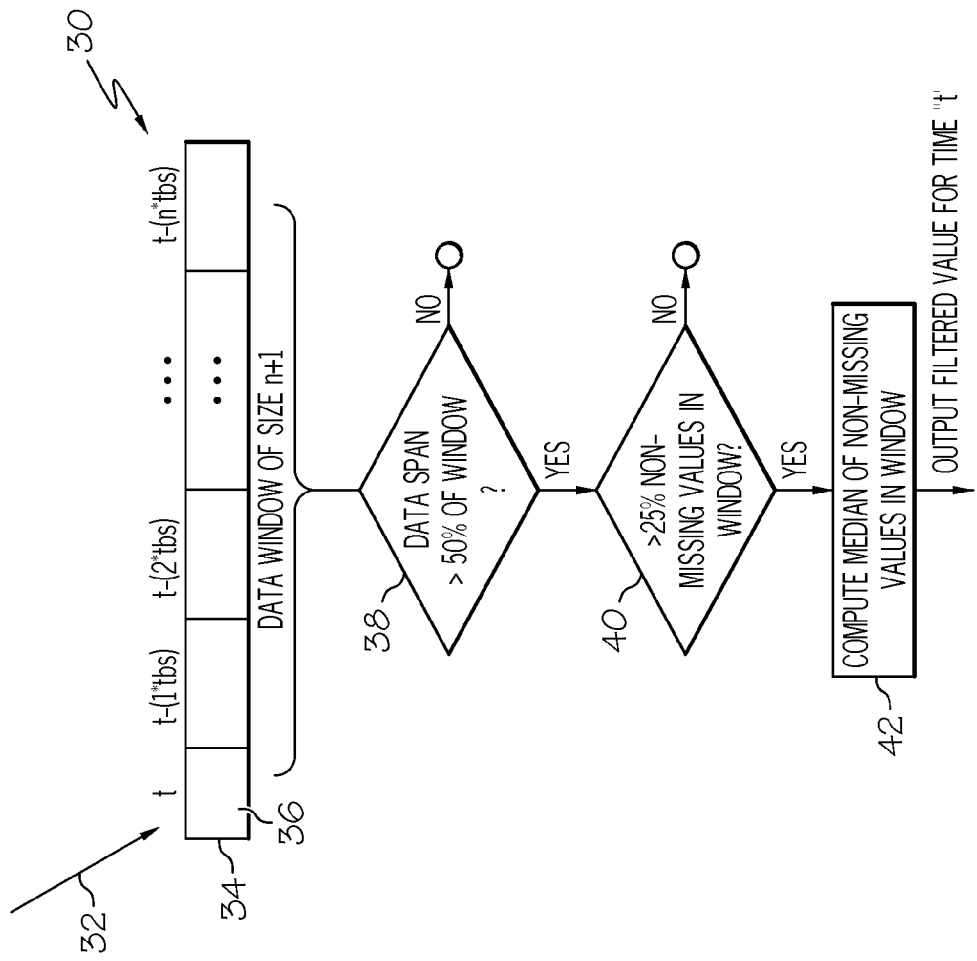
FIG. 3 is a block diagram showing an algorithm used by sliding median filters in the embodiment of FIG. 1.

Referring now to FIG. 3, there is shown a block diagram showing an algorithm 30 used by the sliding median filters 20-1, 20-2, 20-3 and 20-4. As discussed in greater detail below, the algorithm 30 may determine whether the quantity and quality of the data received over a predetermined period of time is adequate for comparing to data limits (for example, in block 16 of FIG. 1) for determining whether to activate an alarm. FIG. 3 shows details for one of the vital sliding median filters 20-1, 20-2, 20-3, 20-4. The detail of FIG. 3 may be replicated for each vital sign that is filtered. While the present invention describes four vital signs being measured, filtered and monitored, any number of vital signs may be included within the scope of the present invention.

Incoming data 32 (corresponding, for example, to one of the data streams 24-1, 24-2, 24-3 or 24-4 of FIG. 2) may be labeled with a time "t", the time of the vital measurement. The current value representing "t" may be moved to the correct position in a holding queue, or data window 34, based on its time. This may result in missing data (slots 36 that are empty), if a time period received no data. Various aspects of the algorithm 30 may be varied. For example, the size of the window 34 may be varied to take data samples over a certain amount of time. Additionally, the sample rate may be varied, which, in turn, may vary the number of samples or slots 36 per data window 34.

The algorithm 30 may, after a data window 34 time period is complete, analyze that data window 34 through various means. For example, the data may be analyzed at block 38 by checking to see if the data span was at least a certain percentage, such as about 50%, of the data window 34. If not, the data from the data window 34 may be discounted for monitoring and alarming, thereby reducing false positive alarms. If block 38 results in a positive answer, then the data may be analyzed by block 40 by checking to see if at least a certain percentage, such as about 25%, of the non-missing values are in the data window 34. If not, the data from the data window 34 may be discounted for monitoring and alarming, thereby reducing false positive alarms. If block 40 results in a positive answer, then, as shown by block 42, a median of non-missing values in the data window 34 may be calculated and sent to the comparative filter 16 (see FIG. 1), via, for example block 26 of FIG. 2.

Embodiments of the present invention may provide the following features:

1. A method of enhancing the sensitivity of means for detecting and alarming on clinical events in patient and physiological monitoring devices that may increase the sensitivity while eliminating the false positives and without introducing an increase in false negatives through an approach of utilizing median filters and sophisticated algorithms;
2. A method to sample the value of a clinical parameter (e.g. heart rate, oxygenation saturation, non-invasive blood pressure, temperature, respiration, but not limited in scope) at a rate substantially greater than the conventional sample rates found in modern monitoring systems, yet averaged over time through the utilization of median filters to increase the alarming accuracy of said parameters;
3. The application of specific median filters to different physiological parameters that may be adjusted for a patients specific disease state or condition based on the patients current status or demographics;
4. The application and adjustment of specific median filters to different physiological parameters that may be adjusted for a patients specific disease state or condition based on the patients current status or demographics as compared to a database containing a huge and varied patient population;
5. Median filters and other low pass filters may be dynamically adjusted during routine monitoring to compensate for artifact and the introduction of drug therapies or other clinical interventions;
6. User intervention can take place to shorten or elongate the sampling times of filters and algorithms based on the patients current status (ex. Ambulatory, conscious sedation or other physiological state);
7. The comparison of several vital sign parameters to dynamically adjust the duration of filtering and to increase accuracy of measurement which may further in turn reduce false positives while not creating false negative alarm states; and
8. The transfer of the output of median filters and algorithms to a single sample representation of the patient's condition over time to a database or data repository which can be used for research purposes.

It should be understood, of course, that the foregoing relates to exemplary embodiments of the invention and that modifications may be made without departing from the spirit and scope of the invention as set forth in the following claims.

We claim:

1. A clinical data monitoring system comprising:
   a sliding median filter assembly disposed for receiving a data stream from a device providing vital signs data, the data stream corresponding to at least one vital sign of a patient being monitored, the median filter assembly configured to:
   detect the data stream within a time window,
   determine whether the detected data stream spans at least a predetermined percentage of the time window,
   determine a false positive reading exists in response to the detected data stream not spanning the at least predetermined percentage,
   ignore the detected data stream for alarming in response to the determination of the false positive reading; and
   output a mean value of the data stream corresponding to the vital sign in response to the detected data stream spanning the at least predetermined percentage;
   a comparative filter disposed for receiving and comparing the mean value output by an algorithm to predetermined data limits; and
   an alert engine disposed for issuing an alarm when the comparative filter has determined that the mean value output is outside of the predetermined data limits.

2. The clinical data monitoring system of claim 1, including at least one device adapted to measure the at least one vital sign and send the data stream to the at least one sliding median filter.

3. The clinical data monitoring system of claim 1, wherein the at least one vital sign includes at least one of heart rate, pulse, oxygen saturation, and respiration rate.

4. The clinical data monitoring system of claim 1, the sliding median filter assembly including a respective sliding median filter for each respective vital sign.

5. The clinical data monitoring system of claim 1, wherein the data stream comprises information about multiple vital signs combined into a single output.

6. The clinical data monitoring system of claim 1, wherein the predetermined data limits are adjustable for a patient specific disease state or condition.

7. The clinical data monitoring system of claim 1, wherein the predetermined data limits are adjustable based on a database containing data representative of a varied patient population.

8. The clinical data monitoring system of claim 1, wherein the sliding median filter assembly is adjustable to compensate for clinical interventions.

9. The clinical data monitoring system of claim 1, wherein the time window is adjustable to reduce false positives.

10. The clinical data monitoring system of claim 1, including a database adapted to receive a single sample representation of a patient's condition over time.

11. A method for monitoring clinical data, the method comprising:
    measuring from a monitoring device at least one vital sign of a patient;

electronically passing a data stream containing the vital sign through a sliding median filter;
detecting with a computing device a portion of the data stream within a time window;
determining in the computing device a percentage of the time window corresponding to non-missing values of the portion of the data stream;
ignoring by the computing device the portion of the data stream when said determined percentage is below a threshold percentage of the time window;
outputting by the device a mean value of the portion of the data stream corresponding to the vital sign, when said determined percentage is at least the threshold percentage of the time window;
comparing by the computing device the mean value output to predetermined data limits; and
issuing by the computing device an alarm when the mean value output is outside of the predetermined data limits.

12. The method of claim 11, including measuring the vital sign over a predetermined duration of time.

13. The method of claim 12, wherein the predetermined duration of time is selected to reduce false positives while not creating false negative alarm states.

14. The method of claim 11, including adjusting the sliding median filter to compensate for clinical interventions.

15. The method of claim 11, wherein the threshold percentage is about 50%.

16. The method of claim 11, wherein the threshold percentage is 25%.

* * * * *